United States Patent [19]

Gruber et al.

[11] 4,144,129
[45] Mar. 13, 1979

[54] CHOLESTEROLOXIDASE AND METHOD FOR ITS PRODUCTION FROM MICROORGANISMS

[75] Inventors: Wolfgang Gruber, Garatshausen; Hans U. Bergmeyer, Tutzing; Michael Nelböck-Hochstetter, Tutzing; Klaus Beaucamp, Tutzing; Günter Holz, Tutzing; Johanna Gramsall, Tutzing; Günter Lang, Tutzing, all of Fed. Rep. of Germany

[73] Assignee: Boehringer Mannheim GmbH, Mannheim-Waldhof, Fed. Rep. of Germany

[21] Appl. No.: 360,490

[22] Filed: May 15, 1973

[30] Foreign Application Priority Data

May 17, 1972 [DE] Fed. Rep. of Germany ....... 2224131
May 17, 1972 [DE] Fed. Rep. of Germany ....... 2224133
Feb. 15, 1973 [DE] Fed. Rep. of Germany ....... 2307518

[51] Int. Cl.$^2$ ............................................. C07G 7/028
[52] U.S. Cl. ........................... 195/66 R; 195/103.5 R
[58] Field of Search .............................. 195/62, 65, 66

[56] References Cited

U.S. PATENT DOCUMENTS

| | | | |
|---|---|---|---|
| 3,607,093 | 9/1971 | Stone | 195/103.5 |
| 3,776,816 | 12/1973 | Terada et al. | 195/66 R |
| 3,907,642 | 9/1975 | Richmond | 195/66 |

OTHER PUBLICATIONS

Turfitt, The Biochemical Journal, vol. 42, pp. 376–383, (1948).
Methods in Enzymology, vol. 22, pp. 214–216, (1971).

*Primary Examiner*—Alvin E. Tanenholtz
*Attorney, Agent, or Firm*—Sprung, Felfe, Horn, Lynch & Kramer

[57] ABSTRACT

A new enzyme, cholesteroloxidase, is prepared by recovering same from microorganisms, preferably by washing a cholesterol-converting microorganism with butanol/water, disintegrating the microorganism culture and extracting same with a buffer solution containing a non-ionic surface-active agent, and isolating cholesterol oxidase from the extract.

19 Claims, No Drawings

CHOLESTEROLOXIDASE AND METHOD FOR ITS PRODUCTION FROM MICROORGANISMS

The invention relates to the production of a new enzyme, cholesteroloxidase. In particular, the invention relates to a method for the recovery of cholesteroloxidase from microorganisms; additionally, the invention is concerned with the culturing of suitable microorganisms, and the use of certain microorganisms as starting material for making such cultures.

It is known that a number of microorganisms are capable of converting cholesterol. For example, Turfitt, in J. Bacteriol. 47, 487 to 493 (1944), describes 188 strains of bacteria which were able to use cholesterol as their sole source of carbon. It was assumed that the decomposition of cholesterol takes place through the coordinated action of a plurality of organisms. It is also known that *Mycobacterium cholesterolicum* grown on glycerin as a source of carbon transforms cholesterol to cholestenone. When this microorganism was made to grow on cholesterol, cholestenedione was mainly formed instead of cholestenone (J. Biol. Chem. 206, 511 to 523 (1954)). Attempts to explain the reaction mechanism have been frustrated by the fact that no soluble enzyme system has been found which would be capable of performing the cholesterol decomposition. Therefore, nothing was known about the enzymes participating in the utilization of cholesterol. However, the discovery of an enzyme for converting cholesterol is desirable, because it is to be expected that it might be useful for a specific method for the determination of cholesterol. Such a specific cholesterol determining method has been lacking hitherto, but would be of great importance in medical diagnosis.

The invention provides a soluble, cholesterol-converting enzyme officially purified to be usable in a routine method of determining cholesterol. The invention also provides particularly suitable microorganisms from which such an enzyme can be produced, and a process for stimulating the formation of the cholesterol-converting enzyme in such microorganisms.

In accordance with the invention an enzyme can be isolated from cholesterol-converting microorganisms, which catalyzes the reaction of cholesterol in accordance with the following equation:

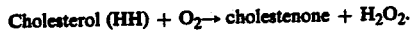

Cholesterol (HH) + $O_2 \rightarrow$ cholestenone + $H_2O_2$.

The enzyme, therefore, is an oxidoreductase with $O_2$ as acceptor. The reaction is stoichiometric, with the formation of $H_2O_2$.

On the basis of the above reaction, the new enzyme has been named cholesteroloxidase.

The activity of the enzyme can easily be determined through the use of the above reaction, for example by determining how much $H_2O_2$ is formed under established conditions. The enzyme is specific and cannot oxidize other steroids. On account of these characteristics, the enzyme is suitable for a specific method of determining cholesterol. Such a method of determination has been lacking heretofore.

The process of the invention for the production of cholesteroloxidase consists in breaking up and extracting a cholesterol-converting microorganism, after washing it with a butanol and water mixture if desired, by destroying the cell wall with a buffer solution containing a non-ionogenic surface-active substance, passing the extract through an anion exchanger, and eluting the enzyme with a fubber solution containing the surface-active substance.

Cholesteroloxidase is an enzyme which on the one hand is bound in the cell membrane of the microorganism and on the other hand has to convert an extremely hydrophobic substance, namely cholesterol. Enzymes of this kind display an especially annoying characteristic in the classical recovery process, viz., they are extremely difficult to release from the membrane, and, even when they have been successfully released, they always tend to clump together and attach themselves to vessel walls, phase interfaces, and even to absorbers and exchanger materials. It is therefore impossible to use conventional methods of enzyme production and isolation. A particular difficulty lies in the fact that the activity and specificity of the enzyme must not be altered.

As mentioned before, any cholesterol-converting microorganism is fundamentally suitable for the performance of the process of the invention. Particularly good results are attained with bacteria of the genus Proactinomyces, and *Proactinomyces erythropolis* NCIB 9158, ATCC 17895 and ATC 4277, and *Nocardia formica* ATCC 14811 are preferred bacteria belonging to this genus. The method of the invention, however, is applicable equally to other microorganisms, bacteria and fungi which are capable of converting cholesterol.

The disintegration of microorganisms by destroying the cell wall with detergents is known in the art, and basically any of the methods described for this purpose and adopted in practice may be used.

The microorganism is broken up and extracted with a buffer solution containing a non-ionogenic surface-active substance. Preferred non-ionogenic surfactants are the alkylarylethyleneglycols and polyethyleneoxide-polypropyleneoxide adducts, especially esters thereof. The concentration of the surfactants to be used in the buffer solution which is to be employed in the disintegration and extraction depends to some extent on the particular surfactant and can be determined by preliminary experiment. In general, concentrations between about 0.01 and 3%, preferably between 0.1 and 1%, are suitable. The buffer solution may have pH values between about 5 and 9, a pH between 6 and 8 being preferred.

The extraction and disintegration in the presence of a surfactant as described results in a specific activity of the desired enzyme 100 times greater than in the case of an extraction performed using the same buffer but with ultrasound instead of the surface-active substance.

Especially good results are obtained when, prior to disintegration and prior to extraction in the presence of the surfactant, the microorganism is subjected to washing with a mixture of butanol and water. Surprisingly, this washing with a butanol-water emulsion does not result in the anticipated clumping or denaturization of the enzyme at boundary surfaces, although in the case of ordinary enzymes which do not have a clumping tendency such washing may of itself result in concentration at boundary surfaces and in a great impairment of activity. In the process of the invention, however, this washing also permits an additional appreciable enrichment of activity. The butanol-water washing can be performed in one or more steps.

The effectiveness of the process steps in accordance with the invention may be demonstrated quantitatively by comparison with a conventional ultrasonic disintegration process. For example, ultrasonic disintegration of a certain quantity of the microorganism with 0.05 M phosphate buffer pH 7.0 makes it possible to obtain 30 units of cholesteroloxidase with a specific activity of 0.01. If, instead, the disintegration of the microorganism is performed with the same buffer with about 0.5% of a surfactant added, a total activity of 60 units and a specific activity of 1.0 are obtained. This corresponds to a doubling of the yield and a 100-fold enrichment. If the latter procedure is repeated, but a washing with butanol-water mixture is performed prior to the disintegration, 60 units of the enzyme are obtained with a specific activity of 3.0 i.e., altogether a 300-fold enrichment.

The extract obtained by the invention, containing the cholesteroloxidase, is then purified by means of ion exchangers. It has been found, however, that it is not possible to follow the conventional methods of such purification, because the enzyme cannot be eluted from the exchanger in such procedures. Even when high ion concentrations were used, the enzyme could not be recovered. Likewise, even with solutions of surface-active substances it was not possible to recover the enzyme. Surprisingly, however, with a combination of buffer and surfactant of relatively low concentration, the enzyme could be washed down virtually completely from the exchanger.

Suitable exchangers are the anion exchangers, especially the weakly basic types. Preferred are exchangers bearing a diethylaminoethanol group. Other exchangers of comparable basicity, however, are also suitable.

The elution from the exchanger is performed preferably with an 0.01 to 0.2 molar buffer solution of the pH range specified above. The concentration of the surfactant then ranges preferably from 0.05 to 2%. Especially preferred is the use of 0.03 to 0.1 molar phosphate buffer with a content of 0.2 to 0.7% of surface-active, non-ionogenic substance.

The enzyme may be isolated from the eluate thus obtained, in a conventional manner, e.g., by precipitation with salts or organic solvents such as ammonium sulfate, methanol and the like. It may also be desirable to precipitate the enzyme from the solution prior to the exchanger chromatography, in order to reduce the amount of solvent. For the redissolving of a precipitated cholesteroloxidase a buffer is preferably used which contains a small amount of a surface-active agent. For it has been observed that the redissolution of the precipitated enzyme sometimes offers great difficulty which is not encountered in the presence of the surface-active agent.

By the process of the invention an approximately 3000-fold enrichment of the enzyme can be performed. Further purification can be achieved by conventional biochemical methods of refinement. When the enzyme is precipitated or adsorbed or bound onto surfaces in such methods, the processes are to be performed in the presence of a surfactant.

The enzyme preparation obtained by the elution of the exchanger can be used directly for the quantitative determination of cholesterol on the basis of the reaction equation given above.

The activity of the enzyme and hence the effectiveness of the process of the invention was determined by measuring the $H_2O_2$ formed in accordance with the above equation by conventional methods of hydrogen peroxide determination.

In the culture of the especially preferred microorganisms mentioned above on cholesterol as the sole source of carbon, the problem exists that cholesterol is only very sparingly soluble in water and consequently collects on the walls of the fermenter. This causes the multiplying microorganisms to become adsorbed and enveloped and thus they escape from the culture solution. The addition of solubilizers such as alcohols or ketones has the disadvantage that these substances are preferred by the microorganism as a carbon source and thus the cholesteroloxidase content is greatly diminished. The addition of conventional emulsifiers led to an inhibition of growth.

This difficulty was overcome in accordance with the invention by letting the microorganisms grow on a mineral salt medium containing peptone and, as soon as the logarithmic growth phase was reached, an aqueous emulsion was added which had been prepared by wet grinding an aqueous cholesterol suspension and then sterilizing it with heat. Thus a 100% utilization of the cholesterol was achieved within a single day of growth at a yield of 1 to 2 g. of pure dry cell substance. The emulsion was added to the culture broth in such a quantity that a total of 1 to 20 g. of cholesterol were added per liter in the course of the growth. The addition is best made portion-wise in accordance with the growth of the microorganisms. A small amount of cholesterol is added to the culture broth preferably at the very beginning of the growth, i.e., before the logarithmic growth phase is reached.

A good nutrient substrate has proven to be an aqueous solution having a pH between 6 and 9 and containing iron chloride and calcium chloride in traces, plus about 0.1 to 2 wt-% peptone, 0.01 to 0.2 wt-% $K_2HPO_4$, 0.05 to 1 wt-% $NH_4H_2PO_4$, and 0.05 to 0.1 wt-% magnesium sulfate heptahydrate. The first addition of cholesterol should be between 0.01 and 0.1%.

In this procedure, specific cholesteroloxidase contents can be achieved of up to about 7 units per gram of dry bacterial mass and about 1 to 3.5 grams of dry bacterial mass per liter of culture medium.

It has furthermore been found that it is possible to increase the cholesteroloxidase content of the said microorganisms severalfold and at the same time to double the dry bacterial mass per liter of culture solution. This is achieved in accordance with the invention by using a microorganism which has first been cultivated on acetate and afterwards on cholesterol, as the sole source of carbon in each case.

This especially preferred embodiment of the invention is based upon the surprising discovery that, by a very special manipulation of the carbon source in the culture medium as defined above, the cholesteroloxidase content of the microorganisms is greatly augmented, and in addition the microorganism yield is substantially increased under otherwise the same conditions, in comparison with the use of peptone as the culture substrate. Thus, if the microorganisms were cultivated on a mineral salt medium of the same composition as described above, but with the peptone replaced by 0.5 wt-% acetate up until the addition of the cholesterol emulsion begins (which occurs when the turbidity is approximately E = 0.25 culture solution diluted 1:20), an increase of the specific activity to 24 units per gram of dry mass was achieved. But at the same time the dry mass content was also increased to 6.5 g/l, an increase of more than 100%.

A substantial further increase of the dry mass content and activity was achieved by adding to the above-described aqueous suspension of cholesterol a small quantity of between 0.02 and 1%, preferably between 0.05 and 0.3 wt-%, of yeast extract as emulsifier.

Good results are achieved in this preferred embodiment of the invention with a content of between 0.1 and 2 w-% of acetate in the form of ammonium acetate. If another acetate is used, such as potassium or sodium acetate, an equimolecular quantity is used.

The main portion of the cholesterol emulsion is added as soon as the logarithmic growth phase is reached, i.e., in the transition from the acceleration to the log phase. This refers to Monod's definition according to which the growth of the microorganisms consists of a leg phase, acceleration phase, log phase and deceleration phase, in that order. The emulsion may be added all at once, batch-wise in several portions, or continuously.

A nutrient substrate especially preferred according to the invention therefore consists of an aqueous solution with a content of about 0.1 to 2 wt-% acetate (as ammonium acetate), 0.01 to 0.2 wt-% $K_2HPO_4$, 0.05 to 1 wt-% $NH_4H_2PO_4$, 0.05 to 0.1 wt-% magnesium sulfate as heptahydrate, iron chloride and calcium chloride in traces, with a pH value between 6 and 9. When the above-defined growth phase is reached, the acetate is replaced with cholesterol. Since the pH value would increase as the culture progressed, acid is added, continuously or in portions, so that the pH value remains virtually constant. Then, during the growth phases in which acetate is the carbon source, acetic acid serves as the acid, and as soon as cholesterol is used, the acetic acid is replaced by a mineral acid. In this second growth stage, hydrochloric acid is preferentially used for pH adjustment.

A continuous culturing performed in two stages, i.e., in two containers, has proven especially desirable, because in this manner optimum cholesteroloxidase activities with reference to the biomass can be achieved. With this preferred embodiment of the invention it has been possible to achieve an activity of up to 30 units per gram of dry mass. In this two-stage, continuous culture method, the average time of stay of the microorganisms in the two stages is best set up so that it will amount in the second stage to 4 to 8 times the first stage. This can be achieved simply by making the capacity of the second-stage tank 4 to 8 times that of the first-stage tank while keeping the throughput constant. The best average detention times, however, varied to a certain extent with the different microorganisms and are best determined for special microorganisms by preliminary experiment. It proved to be generally desirable to use two tanks in series, with a throughput of 0.25 to 0.30 volume per hour in the first stage and of 0.055 to 0.065 volume per hour in the second stage, the cholesterol emulsion being added in the second tank.

The following examples will further explain the invention.

EXAMPLE 1

2 Liters of a nutrient substrate consisting of 0.5-% casein peptone, 0.05 wt-% $K_2HPO_4$, 0.2 wt-% $NH_4H_2PO_4$, 0.02 wt-% magnesium sulfate heptahydrate, iron chloride and calcium chloride in traces in tap water, adjusted to pH 7.5 with KOH, were inoculated in a shaking flask with 200 ml. of a well grown preliminary culture of Proactinomyces erythropolis NCIB 9158 and heavily aerated on a magnetic stirrer. When the logarithmic growth phase began, which can be recognized from the increase in turbidity, a cholesterol suspension, prepared by wet grinding and sterilization, was added portion-wise as growth continued in such a manner that, within 20 hours, a total amount of 10 g. of cholesterol entered the flask. 5 hours after the last cholesterol addition, the cell mass was harvested by centrifugation. 4 g. of dry bacterial mass was obtained. After disintegration with ultrasound, 3 units per gram of cholesteroloxidase were obtained, one unit corresponding to the formation of 1 micromole of $H_2O_2$ per minute equal to oxidation of 1 micromole of cholesterol per minute under the following test conditions:

2.31 ml $PO_4$ buffer, 0.05 M, pH 7.0 (+ chromogen 2 ml., c = 50 to 100 ml. buffer)
0.05 ml. cholesterol solution, c = 3.7, in t-butanol
0.6 ml. t-butanol, 0.02 ml. POD, c = 1, 0.02 ml. bacteria extract.

EXAMPLE 2

In a suitable culture vessel, 15 liters of the medium described in Example 1 were cultivated with 0.5 liter of well grown preliminary culture of P. erythropolis ATCC 17895, with strong aeration. In this case, 0.05% cholesterol was added right at the beginning. Upon the commencement of the logarithmic growth (criterion as in Example 1), sterilized cholesterol suspension was continuously added as growth progresses, so that a total amount of 50 g. of cholesterol went into the fermenter in 15 hours of culture time. A bacterial mass of 40 g. was thus obtained 7.1 units per gram of cholesteroloxidase were obtained by ultrasonic disintegration from the bacterial mass.

EXAMPLE 3

P. erythropolis (NCIB 9158) was cultivated as described in Example 2 in a working volume of 60 liters. After about 25 hours (i.e., at the harvest time of Example 2) the feeding of fresh nutrient medium to the culture vessel was begun, while grown culture solution was taken from the vessel in the same amount. The dilution rate (rate of flow per working volume) amounts in this case to 0.04. At the same time cholesterol suspension was fed to the fermenter such that about 3 g. of cholesterol was added per hour. Thus, in continuous culture, a yield of 1.2 to 1.5 g. of dry bacterial per liter was obtained with the same specific activity as was obtained in the batch process described in Example 2.

EXAMPLE 4

In a 20-liter fermenter, 15 liters of culture substrate, consisting of 0.5 wt-% ammonium acetate, 0.05 wt-% secondary potassium phosphate, 0.2 wt-% primary ammonium phosphate, 0.02 wt-% magnesium sulfate heptahydrate and traces of iron chloride and potassium chloride in tap water, were inoculated with 0.5 liter of a well-grown preliminary culture of Proactinomyces erythropolis NCIB 9158 and cultivated with strong aeration (600 liters of air per hour, stirrer speed 600 rpm, stirrer paddle diameter 120 mm). The pH value of the culture was kept constant by the continuous addition of 20% acetic acid until the biomass concentration was about 1.5 g./l., which corresponded to a turbidity of G = 0.250 in a culture broth diluted 1:20.

After this concentration was reached, sterilized cholesterol suspension was added continuously as the culture continued, such that a total amount of 30 g. of cholesterol entered the fermenter in 20 hours of culture. The cholesterol suspension contained 0.1 to 0.2% yeast extract. Dilute hydrochloric acid was now used for neutralizing the culture instead of acetic acid. At the end of the cultivation the biomass was separated from the culture solution by centrifugation and 2.6 g. of dry mass per liter was obtained with an activity of 12 units per gram of dry mass.

EXAMPLE 5

In a two-stage continuous culture process, two fermenters with a working volume of 15 liters for the first stage and 70 liters for the second stage were combined such that, at an hourly throughput of 4 liters of the nutrient substrate described in Example 1, a throughput rate of 0.25 to 0.30 volumes will prevail in the first stage and a throughput rate of 0.055 to 0.65 volumes will prevail in the second stage. At the beginning of the cultivation the second stage was inoculated with 1.5 liters of a well-grown preliminary culture of *Proactinomyces erythropolis* (ATC 17895) and the first stage with 0.5 liters of the same preliminary culture (at 5 hours apart from one another). With intense aeration of both stages as described in Example 4, cultivation was conducted until the growth criteria specified in Example were satisfied, the first stage being neutralized with acetic acid and the second stage with hydrochloric acid.

At the same time, a continuous addition of cholesterol emulsion of the same kind as described in Example 4 was begun in the same manner as in Example 4, and the throughput of 4 liters of nutrient medium per hour was established. The pH values were maintained at 7 to 7.5. Thus, 4 liters per hour were obtained of a culture broth containing about 7 g. of dry mass per liter with an activity of 40 units per gram of dry mass. The culture solution was collected in a refrigerated storage tank and from time to time the bacterial mass was separated from it with a flow-through centrifuge. Approximately 10 g. of 100% acetic acid was needed per hour in the first stage for pH control.

EXAMPLE 6

40 ml. of n-butanol was added to 40 ml. of a suspension of Nocardia erythropolis (approx. 10 g. dry weight) and stirred for a few minutes at room temperature. The mixture was centrifuged and both the butanol and the supernatant aqueous phase were poured off. 40 ml. of water was added to the sediment and, after a homogeneous suspension of the cells had been prepared, 40 ml. of n-butanol was again added, the suspension was stirred for a few minutes at room temperature, and then centrifuged. The sediment was suspended in 40 ml. of 0.01 molar phosphate buffer, pH = 7.0, to which 0.3% of a nonionogenic surface-active agent (alkylaryl polyethylene glycol) had been added, and the suspension was stirred at room temperature for 30 minutes. Then it was centrifuged and the sediment was discarded. The extract contained about 120 units of cholesteroloxidase with a specific activity of 3 units per ml. of protein.

Solid ammonium sulfate was added to this extract at 0° C. up to an ammonium sulfate concentration of 1.3 M. Then the suspension was centrifuged, the sediment gathering on the surface of the solution on account of an apparently lipophilic content. The caked sediment was filtered, dissolved with 0.01-molar phosphate buffer, pH = 7, and then exhaustively dialyzed against the same buffer at 0° C.

The dialyzed solution was absorbed into a column balanced with 0.01-molar phosphate buffer, pH = 7, in a regular commercial anion exchanger with diethylaminoethanol groups on a dextran basis. The enzyme was adsorbed. After the column had been washed with the same buffer, it was washed successively with solutions of 0.5%, 2% and 5% of the above-mentioned surface-active agent in water, whereupon large amounts of impurities were eluted. Then it was washed successively with 0.01 M phosphate buffer, pH 7, 0.2 M phosphate buffer, pH 7 and 0.5 M phosphate buffer, pH 7. Then it was washed again with 0.05-molar phosphate buffer pH 7, and then the desired enzyme was eluted with 0.05-molar phosphate buffer to which 0.5% of surface-active agent had been added. The eluate contained about 80% of the cholesteroloxidase enzymatic activity adsorbed on the column, having a specific activity of 25 to 30 units per mg. of protein.

EXAMPLE 7

The process of Example 6 was repeated, except that the washing with butanol and water was omitted. An extract for the ammonium sulfate precipitation was thus obtained, which contained about 120 units of cholesteroloxidase with a specific activity of 1 unit per mg. of protein.

EXAMPLE 8

(for purposes of comparison)

The process of Example 6 was repeated, except that the elution of the exchanger was performed with an aqueous solution containing 5% of the same surface-active agent dissolved therein. No enzymatic activity could be washed back out of the column. The enzyme attached itself irreversibly to the exchanger.

It will be understood that the specification and examples are illustrative but not limitative of the present invention and that other embodiments within the spirit and scope of the invention will suggest themselves to those skilled in the art.

What is claimed is:

1. Process for the preparation of cholesteroloxidase, which process comprises culturing a cholesterol-converting microorganism, disintegrating the culture and extracting same with a buffer solution containing a non-ionic surfactant, by means of destruction of the cell walls, and isolating cholesteroloxidase from the extract.

2. Process as claimed in claim 1, wherein the extract is passed through an anion exchanger and the enzyme is eluted with a buffer solution containing the surfactant, to effect the isolation of cholesteroloxidase.

3. Process as claimed in claim 1, wherein the cholesterol-converting microorganism culture is washed with butanol and water prior to said disintegration.

4. Process as claimed in claim 1, wherein the cholesteroloxidase is precipitated from the extract by the addition of ammonium sulfate and is then re-absorbed in a buffer solution.

5. Process as claimed in claim 4, wherein a buffer solution of pH 5 to 9 is used.

6. Process as claimed in claim 2, wherein the enzyme is eluted from said anion exchanger with a 0.01 to 0.28 x molar buffer solution.

7. Process as claimed in claim 1, wherein the microorganism is *Proactinomycetes erythropolis* NCIB 9158.

8. Process as claimed in claim 1, wherein the microorganism is *Proactinomycetes erythropolis* ATCC 17895.

9. Process as claimed in claim 1, wherein the microorganism is *Proactinomycetes erythropolis* ATCC 4277.

10. Process as claimed in claim 1, wherein the microorganism is *Nocardia formica* ATCC 14811.

11. Process as claimed in claim 1, wherein said microorganism is cultured on cholesterol as its sole source of carbon by adding to the microorganism, cultured on mineral salt medium containing peptone or acetate as the sole carbon source, an emulsion prepared by wet grinding an aqueous cholesterol suspension and then sterilizing the emulsion by heating, which adding step is effected as soon as the logarithmic growth phase has been reached, and continuing cultivation on cholesterol as the sole source of carbon.

12. Process as claimed in claim 11, wherein a total of 1 to 20 grams of cholesterol is added per liter of culture broth.

13. Process as claimed in claim 11, wherein the microorganism is permitted to grow on acetate as the sole source of carbon until the transition from the acceleration phase to the log phase.

14. Process as claimed in claim 11, wherein a cholesterol emulsion stabilized with yeast extract is used.

15. Process as claimed in claim 11, wherein the microorganism is cultured continuously in two tanks connected in series, with an average detention time in the second stage which is four to eight times greater than the average detention time in the first stage, and wherein the cholesterol emulsion is added in the second stage.

16. A method of preparing an enzyme preparation having cholesterol oxidase activity, which comprises growing a Nocardia species in a suitable medium, harvesting the cells, extracting said cells with a surface active agent and recovering therefrom an enzyme preparation having a cholesterol oxidase specific activity and capable of oxidizing cholesterol to cholestenone and hydrogen peroxide.

17. A method as claimed in claim 16 in which said surface active agent is a non-ionic surface active agent.

18. A method as claimed in claim 16 in which said surface active agent is an alkylaryl polyethylene glycol.

19. A method of preparing an enzyme preparation having cholesterol oxidase activity, which comprises aerobically growing a Nocardia species in a medium comprising a carbon source and in which growth is carried out in the presence of cholesterol, harvesting the cells, extracting said cells with a surface active agent and recovering an enzyme preparation having a cholesterol oxidase specific activity and capable of oxidizing cholesterol to cholestenone and hydrogen peroxide.

* * * * *